US012766338B2

(12) United States Patent
Shavit

(10) Patent No.: US 12,766,338 B2
(45) Date of Patent: *Oct. 20, 2026

(54) DEVICES AND METHODS FOR STIMULATING TEAR SECRETION

(71) Applicant: Demaod Ltd, Tel Aviv (IL)

(72) Inventor: Ronen Shavit, Tel Aviv (IL)

(73) Assignee: Demaod Ltd, Tel Aviv (IL)

( * ) Notice: Subject to any disclaimer, the term of this patent is extended or adjusted under 35 U.S.C. 154(b) by 202 days.

This patent is subject to a terminal disclaimer.

(21) Appl. No.: 18/891,929

(22) Filed: Sep. 20, 2024

(65) Prior Publication Data

US 2025/0010097 A1 Jan. 9, 2025

Related U.S. Application Data

(63) Continuation of application No. 18/159,978, filed on Jan. 26, 2023, now Pat. No. 12,472,376.

(30) Foreign Application Priority Data

Feb. 6, 2022 (IL) .......................................... 290389
Jun. 30, 2022 (IL) .......................................... 294455

(51) Int. Cl.
*A61N 5/06* (2006.01)
*A61H 23/02* (2006.01)

(52) U.S. Cl.
CPC ........... *A61N 5/0622* (2013.01); *A61H 23/02* (2013.01); *A61H 2201/10* (2013.01);
(Continued)

(58) Field of Classification Search
CPC .......... A61N 5/0622; A61N 2005/0626; A61N 2005/0648; A61N 2005/0661;
(Continued)

(56) References Cited

U.S. PATENT DOCUMENTS 5,384,593 A 1/1995 Gell
6,210,000 B1 4/2001 Yee
(Continued)

FOREIGN PATENT DOCUMENTS

CN 102846423 B 5/2017
EP 3349848 A1 7/2018
(Continued)

OTHER PUBLICATIONS

American National Standards Institute. ANSI Z136.1-2000 Standard. https://www.lia.org/resources/laser-safety-information/laser-safety-standards/ansi-z136-standards. Accessed Jan. 25, 2023.
(Continued)

*Primary Examiner* — Jonathan T Kuo
(74) *Attorney, Agent, or Firm* — IPTechLaw

(57) ABSTRACT

In various implementations, a device for stimulating the lacrimal gland and optionally the meibomian gland of an eye of a user by emitting light on the retina may include a control unit and an optical system connected to the control unit and arranged in the viewing direction of the user. Implementations of the device may also include a power supply unit for supplying power to the control unit and/or optical system. The light stimulation pulses activate the pupillary light reflex and one or more reflexes selected from blink reflex, corneal reflex, menace reflex, and lacrimal reflex.

10 Claims, 7 Drawing Sheets

(52) U.S. Cl.
CPC ................ *A61H 2201/1604* (2013.01); *A61H 2201/165* (2013.01); *A61H 2201/5048* (2013.01); *A61H 2201/5092* (2013.01); *A61H 2205/022* (2013.01); *A61N 2005/0626* (2013.01); *A61N 2005/0648* (2013.01); *A61N 2005/0661* (2013.01); *A61N 2005/0663* (2013.01)

(58) Field of Classification Search
CPC .... A61N 2005/0663; A61N 2005/0662; A61N 2005/0667; A61H 23/02; A61H 2201/10; A61H 2201/1604; A61H 2201/165; A61H 2201/5048; A61H 2201/5092; A61H 2205/022; A61H 5/00
See application file for complete search history.

(56) References Cited

U.S. PATENT DOCUMENTS

| | | | |
|---|---|---|---|
| 10,258,809 | B2 | 4/2019 | Friedman |
| 11,181,740 | B1 | 11/2021 | Lewis |
| 2003/0056281 | A1 | 3/2003 | Hasegawa |
| 2008/0259098 | A1 | 10/2008 | Zamorsky |
| 2014/0330129 | A1 | 11/2014 | Grenon et al. |
| 2015/0100001 | A1 | 4/2015 | Bujak |
| 2015/0174425 | A1 | 6/2015 | Toyos et al. |
| 2016/0022135 | A1 | 1/2016 | Agarwal |
| 2018/0116872 | A1 | 5/2018 | Kahook |
| 2018/0304079 | A1 | 10/2018 | Kim et al. |
| 2018/0344512 | A1 | 12/2018 | Badawi |
| 2019/0091065 | A1 | 3/2019 | Kelleher |
| 2020/0146881 | A1 | 5/2020 | Linder et al. |
| 2020/0205657 | A1 | 7/2020 | Li et al. |
| 2020/0360723 | A1 | 11/2020 | Azar et al. |
| 2021/0008379 | A1 | 1/2021 | Ackermann et al. |
| 2021/0052216 | A1 | 2/2021 | Badawi |
| 2021/0138232 | A1 | 5/2021 | Paz et al. |
| 2021/0178178 | A1 | 6/2021 | Tedford |
| 2021/0187320 | A1 | 6/2021 | Pomar |

FOREIGN PATENT DOCUMENTS

| | | | |
|---|---|---|---|
| EP | 3838341 | A1 | 6/2021 |
| JP | 4242195 | B2 | 3/2009 |
| JP | 5137956 | B2 | 2/2013 |
| KR | 20150006684 | A | 1/2015 |
| KR | 20170021526 | A | 2/2017 |
| KR | 101776226 | B1 | 9/2017 |
| KR | 101820928 | B1 | 3/2018 |
| KR | 20200141804 | A | 12/2020 |
| KR | 20210019619 | A | 2/2021 |
| KR | 20210027842 | A | 3/2021 |
| WO | 2017167939 | A1 | 10/2017 |
| WO | 2020198444 | A1 | 10/2020 |
| WO | 2021086924 | A1 | 5/2021 |

OTHER PUBLICATIONS

Butcher et al. The Physical Properties of Human Sebum. The Journal of Investigative Dermatology, 12(4), Apr. 1949, 249-254. PMID: 18120703.

Chemistry of Vision. Chemistry LibreTexts. 2016. https://chem.libretexts.org/Bookshelves/Biological_Chemistry/Supplemental_Modules_(Biological_Chemistry)/Photoreceptors/Chemistry_of_Vision. Accessed Jan. 25, 2023.

Craig et al. The Ocular Surface. Tfos Dews Ii Definition and Classification Report, The Ocular Surface, 15(3), Jul. 2017, 276-283, https://doi.org/10.1016/j.jtos.

Dartt. Neural Regulation of Lacrimal Gland Secretory Processes: Relevance in Dry Eye Diseases, Progress in Retinal and Eye Research, 28(3), May 2009, 155-177. doi: 10.1016/j.preteyeres.

De Souza et al. Age-Related Autoimmune Changes in Lacrimal Glands. Immune Network, 19(1), Feb. 2019. https://doi.org/10.4110/in.2019.19.e3.

Delori et al. Maximum Permissible Exposures for Ocular Safety (ANSI 2000), with Emphasis on Ophthalmic Devices. Journal of the Optical Society of America A 24, Jun. 2007, 1250-1265. doi: 10.1364/JOSSA.24.001250.

Lobato-Rincon et al. Pupillary Behavior in Relation to Wavelength and Age. Frontiers in Human Neuroscience, 8:221, Apr. 2014, 1-8. doi: 10.3389/fnhum.2014.00221.

Murube. Sources In Time: Basal, Reflex, and Psycho-emotional Tears. The Ocular Surface, 7(2), Apr. 2009, 60-66. doi: 10.1016/s1542-0124(12)70296-3. PMID: 19383274.

Rocha et al. The Aging Lacrimal Gland: Changes in Structure and Function. The Ocular Surface, 6(4), Oct. 2008, 162-174. doi: 10.1016/s1542-0124(12)70177-5. PMID: 18827949; PMCID: PMC4205956.

Scenihr. Scientific Committee on Emerging and Newly Identified Health Risks, Potential Health Risks of Exposure to Noise from Personal Music Players and Mobile Phones Including a Music Playing Function. European Commision, Directorate-General for Health & Consumers, 2008, 1-81. https://ec.europa.eu/health/ph_risk/committees/04_scenihr/ docs/scenihr_o_017.pdf.

Yan et al. Maintaining Ocular Safety with Light Exposure, Focusing on Devices for Optogenetic Stimulation. Vision Research. Apr. 2016, 121:57-71, 1-45. doi: 10.1016/j.visres.2016.01.006. Epub Feb. 26, 2016. PMID: 26882975; PMCID: PMC4813666.

European Search Report, 23749434.9, European Patent Office, Nov. 25, 2025.

DEVICES AND METHODS FOR STIMULATING TEAR SECRETION

CROSS REFERENCE TO RELATED APPLICATIONS

This document is a continuation of U.S. patent application Ser. No. 18/159,978 entitled "Devices and Methods for Stimulating Tear Secretion" to Ronen Shavit which was filed on Jan. 26, 2023, which application claims priority to Israeli Patent Application Nos. 290389 filed on Feb. 6, 2022 and 294455 filed on Jun. 30, 2022, the disclosures of each of which are hereby incorporated entirely herein by reference.

FIELD OF THE INVENTION

The invention relates to dry eye diseases, in general, and to devices and methods for stimulating tear secretion, in particular.

BACKGROUND OF THE INVENTION

Dry eye is defined as a disorder of the tear film due to insufficient tear production or excessive tear evaporation. The symptoms can manifest as mild discomfort, or burning at varying intensity, foreign body sensation, dryness, photophobia. In severe cases, the disease can progress to affect the corneal tissue and determine ulcers, infiltrates, visual disturbances. Aging and female gender are risk factors for dry eye disease. At any age, about twice as many women as men have dry eye. The aging process appears to significantly affect dry eye disease (DED).

The aging-dependent changes in the ocular surface with DED are related to biological changes in the lacrimal glands (LGs) and meibomian glands (MGs). The lacrimal glands are paired exocrine glands, one for each eye, that secrete the aqueous layer of the tear film. In humans, they are situated in the upper lateral region of each orbit, in the lacrimal fossa of the orbit formed by the frontal bone. The lacrimal gland (LG) plays a vital role in the maintenance of ocular physiology and changes related to aging directly affect eye diseases. The dysregulation of the immune system in aging leads to quantitative and qualitative changes in antibodies, cytokines, proteins, vitamins. The tear film contains between several dozens to several hundred proteins and other chemical molecules such as: Electrolytes (sodium, potassium, chloride, bicarbonate, magnesium, and calcium), Proteins (lysozyme, lactoferrin, lipocalin, IgA, EGF, and other growth factor, etc.), Lipids, Mucins and vitamins.

The aged lacrimal gland affects the initial chemical composition of the tear film therefore affects the functionality of the eye and the eyelid. One aspect of the aged lacrimal gland is a gradual decline of the immune system, there is an increase in autoimmunity, with a reciprocal pathway between low levels of inflammation and aging mechanisms. The aging of the lacrimal gland is related to functional changes, reduced innervation, and decreased secretory activities. Lymphocytic infiltration, destruction, and atrophy of glandular parenchyma, ductal dilatation, and secretion of inflammatory mediators modify the volume and composition of tears.

Meibomian glands (also called tarsal glands, palpebral glands, and tarsoconjunctival glands) are sebaceous glands along the rims of the eyelid inside the tarsal plate. They produce meibum, an oily substance that prevents evaporation of the eye's tear film.

In accordance with TFOS-II, dry eye disease is divided into two types: tear deficient; and evaporative. In most cases, tear deficiencies are a result of lacrimal gland malfunctioning. The evaporative dry eye is associated with meibomian gland dysfunction. (J. P. Craig, K. K. Nichols, E. K. Akpek, B. Caffery, H. S. Dua, C. Joo, M D, Z. Liu, J. D. Nelson, J. J. Nichols, K. Tsubota, F. Stapleton, TFOS DEWS II Definition and Classification Report, The Ocular Surface Volume 15, Issue 3, July 2017, Pages 276-283, https://doi.org/10.1016/j.jtos.2017.05.008).

In accordance with Dartt the activation of the lacrimal gland is also controlled by the activation of sensory nerves in the corneal and conjunctival epithelia (D. A. Dartt, Neural Regulation of Lacrimal Gland Secretory Processes: Relevance in Dry Eye Diseases, Prog Retin Eye Res. 2009 May; 28(3): 155-177. doi:10.1016/j.preteyeres.2009.04.003). Quoting Dartt "The first segment of the lacrimal gland functional unit that regulates lacrimal gland secretion is the activation of sensory nerves in the corneal and conjunctival epithelia. The ocular surface epithelia are richly endowed with sensory nerve endings that respond to changes in the environment causing a rapid secretion of lacrimal gland fluid to wash away and chemically neutralize foreign substances that have entered the tear film. Stimulation of corneal sensory nerves causes fluid secretions and vasodilation in the lacrimal gland. Lacrimal gland fluid secretion is dependent upon vasodilation with increased blood flow augmenting secretion and decreasing blood flow inhibiting stimulated secretion." Dartt states that the mechanism responsible for the coupling between lacrimal gland vasodilation and fluid secretion is unknown.

The conventional therapy suggested by the US National Eye Institute for treating DED includes: over-the-counter eye drops (artificial tears) or moisturizing gels and anti-inflammatory topical formulations; prescription medicines such as cyclosporine (Restasis) or lifitegrast (Xiidra); and lifestyle changes such as avoiding smoke, wind, and air conditioning.

A traditional homemade remedy is to apply warm compresses to the eyes. In accordance with Butcher et. al (BUTCHER E O, COONIN A. The physical properties of human sebum. J Invest Dermatol. 1949 April; 12(4):249-54. PMID: 18120703.), human sebum viscosity vs. temperature can be linear and approximate. At 37° C., the viscosity is about 600 millipoises, and at 27° C., the viscosity is about 1,000 millipoises. as meibum may be approximate as sebum, we may conclude that even slight heating of the meibum by contacting the eyelid skin may lead to a substantial decrease of the meibum viscosity, therefore, may lead to improved flow of meibum within the meibomian gland and therefore relief the symptoms of dry eyes and meibomian gland dysfunction (MGD). Heating of the eyelid skin of the epithelium layer may be done by direct contact as previously presented by Alcon Systane® iLux2®. In another case, a combination of heat and pressure is aimed to obtain similar results as demonstrated by JNJ Lipiflow. Using the Lipiflow, the eyelid is heated to about 40° C.; therefore, the meibum temperature is elevated, resulting in a change in meibum viscosity. MGD is thus relieved by making the meibum more flowable. The combination of lower meibum viscosity with an external pressure applied by the device provides meibum that may flow easily; hence the flow of meibum is restored.

Many patent publications suggest devices based on this traditional remedy, one of which is US Patent Application Publication No. 20180344512 which describes dry eye treatment apparatus which comprises a patch or strip affixed to the skin of the upper and/or lower eyelids to deliver heat or other forms of energy to the one or more meibomian glands contained within the underlying skin of the eyelid of a subject. Additional devices are disclosed in CN102846423, JP5137956, US20200146881 and US20210052216.

Another dry eye treatment strategy known in the art proposes electrical nerve stimulation of the lacrimal gland through electrodes which are implanted in the eye. Such implants are described in EP 3349848, WO2017072575, US20180116872, WO2020198444 and WO2021086924. This is an invasive method which does not suit everyone. US2021138232 describes transcutaneous nerve stimulation such as facial nerve stimulation for artificially eliciting eye blink, such as with humans with acute facial paralysis (Bell's palsy or Dry Eye syndrome). US20150100001 discloses therapeutic ultrasound device for treating an eye condition.

JP 4242195 discloses an optical treatment appliance which accelerates the secretion of tears by stimulating the lacrimal gland. The appliance is equipped with a probe which irradiates light from its tip when in contact with the vicinity of the lacrimal gland on the upper part of the eyelid. The probe is equipped with a touch sensor and the treatment is performed without irradiating the eyeball.

Eyelid illumination with an infrared (IR) light for imaging meibomian glands for meibomian gland analysis is disclosed in US20140330129 and KR 101776226.

KR1020210027842 discloses an ophthalmic wearable treatment device comprising: a part wearable on a user's head, a light irradiation part and irradiating light having a wavelength absorbable into the user's eyelid tissue. The treatment light irradiated by the light irradiation unit is absorbed by the eyelid tissue and converted into thermal energy to treat dry eye syndrome, thereby dissolving lipid residues or wastes formed in the secretion path to secure a discharge path. The treatment light has a wavelength band having excellent absorption characteristics by lipids (900 nm to 950 nm, or 1140 nm to 1260 nm). The device includes a detection unit for detecting real-time position information of the eyelid so that the treatment can be performed in response to situation in which a patient moves the eyelid.

Thus, prior art methods and devices for treating dry eye syndrome suggest one of the following: pharmaceutical compositions required to be administered to the eye very often during the day and usually in long term use lose effectiveness; medical implants; medical devices that treat the eyelid or the skin in vicinity of the lacrimal glands and/or meibomian glands by transferring light energy which transforms into heat energy in order to artificially stimulate the glands to secret tears or sebum. The treatment is provided mainly wherein the eyeball is covered and requires a direct contact of the probe with the skin.

This is where the present invention starts. It is therefore an object of the present invention to suggest alternative options for treating DED. The invention aims at providing a device for stimulating the lacrimal gland and/or meibomian gland in a more natural approach. A device that is, on the one hand, safe and easy to use, and on the other hand does not stress the body or harm tissues. Moreover, some embodiments of the device of the present invention may contribute to the adherence of the user to the therapeutic regimen because of their experience of virtual reality during the use. The current invention also aims at activating the blink reflex and the lacrimal reflex in order to re-balance the gland function and restore, at least partially, the initial chemical composition of the tears necessary for the regular function of both the lacrimal and meibomian glands.

SUMMARY OF THE PRESENT INVENTION

The present invention pertains to a device for stimulating the lacrimal gland and/or meibomian gland of an eye of a user.

By emitting light on the retina, the device may change tear chemical composition and may induce severe meibum secretion by re-activating the aged lacrimal gland. The device includes a control unit and an optical system connected to said control unit and arranged in the viewing direction of the user. The optical system includes at least one light source and is configured for providing light stimulation pulses to an eye of the user by at least one light source. The device also includes a power supply unit for supplying power to said control unit and/or said optical system. The stimulation pulses activate the pupillary light reflex and one or more reflexes selected from: blink reflex; corneal reflex, menace reflex; and lacrimal reflex. Activation of each one of these reflexes or a combination thereof with the pupillary light reflex prevents any potential damage to the eye. Furthermore, such activation induces blinking of the eye of the user and thereby self-regulation of the tear mechanism resulting natural secretion of tears and relief of dry eye symptoms. It may also improve the ability of the lacrimal gland to reproduce more chemically balanced proteins and other molecules such as vitamin A. In addition, it should be emphasized that blinking and pupillary light reflex are activated without a direct contact with the eye or eyelids.

In an aspect of the invention, there is provided a device for stimulating the lacrimal gland and/or meibomian gland of an eye of a user by emitting light on the retina, the device comprising a control unit; an optical system connected to said control unit and arranged in the viewing direction of the user, said optical system includes at least one light source, and is configured for providing light stimulation pulses to an eye of the user by said at least one light source; and a power supply unit for supplying power to said control unit and/or said optical system; wherein said light stimulation pulses activate the pupillary light reflex and one or more reflexes selected from: blink reflex; corneal reflex; menace reflex; and lacrimal reflex, wherein when said device is in operation mode a light intensity gradient between the light pulses emitted by said at least one light source and the light around the eye is maintained at least 2 lumens, and wherein said light stimulation pulses induce blinking of the eye of said user. The device operates without physical contact with the eyes or eyelids. An embodiment of the invention may be a non-thermal device which uses wavelength limited to the visible light.

In one or more embodiments, the control unit may be a personal computer, laptop, tablet, mobile phone or a microprocessor wired or wirelessly connected to said optical system. The control unit is programmed to actuate the optical system and any other stimulation pulses and stimulation components integrated in the device. In one or more embodiments, the power supply unit may be integrated with or arranged within the optical system. In other embodiments, the power supply unit may be integrated with or arranged within the control unit and also supply power to the optical system. Alternative embodiments of the device may be constructed to connect with an external power supply unit or even plug to domestic power via a wire/adapter.

In one or more embodiments, the device may further comprise coupling means for releasably coupling the device with a headset or conventional eye or sun glasses. In some alternative embodiments, the device is structured as a headset configured to interconnect with and accommodate a mobile phone such that the display screen of the mobile phone is facing the user's eyes. In one or more embodiments, the at least one light source emits light of wavelength band of 350 nm to 750 nm. In some embodiments, the light source provides light stimulation pulses in a random pattern in order to prevent the development of endurance of the eye. The light source generates light stimulation pulses in a random pattern that surprises the user. In one or more embodiments, the optical system further comprises lens, adjustable lens and/or lens adjusting mechanism.

In one or more embodiments, the device may further comprise a sound source operable by the control unit. In one or more embodiments, the device may also comprise a vibration source operable by the control unit. In one or more embodiments, the device further comprise means for producing eyelash disturbance, operable by the control unit. In one or more embodiments, the device may further comprise a rotating element positioned in the line of sight of a user and electrically connected to said power supply and configured to allow light passage through a lumen positioned in the outer surface thereof towards the eye of said user.

In one or more embodiments, the device may further comprise means for providing air flow towards the eyes of the user. In one or more embodiments, the device may further comprise means for providing water drops towards the eye of the user. In one or more embodiments, the optical system further comprises a shading element operable by the control unit and powered by the power supply unit, the shading element is configured to block and un-block light from the eye of the user during the operation mode of the device. In one or more embodiments, the device further comprises a combination of at least two of the following: sound source, vibration source, means for producing eyelash disturbance, a rotating element, means for providing air flow, means for providing sterile or non-sterile liquid drops i.e., water, saline, water for injection and a shading element.

In one or more embodiments, the device may further comprise a camera for capturing the eye reaction to the stimulation pulses and transferring the captured data to the control unit for analysis. In one or more embodiments, the control unit is configured to interconnect with a virtual reality (VR) like headset or augmented reality (AR) like headset or mixed reality (MR) headset, or any other smart headset unit which can be placed on a face of the user. In one or more embodiments, the control unit is further programmed to interconnect with said smart headset unit to display a sequence of pulses and or pictures in a desired pattern towards the eye of the user, wherein said pictures induce blinks of the eye of said user.

The present invention, in some embodiments relates to kits for stimulating dry eyes. In some embodiments of the invention a kit for stimulating the lacrimal gland and/or meibomian gland of an eye of a user includes a device for stimulating the lacrimal gland and/or meibomian gland of an eye of a user and coupling means for releasably coupling the device with a conventional eye or sun glasses. In some embodiments, the device includes a control unit and an optical system connected to the control unit and arranged in the viewing direction of the user. The optical system includes at least one light source, and is configured for providing light stimulation pulses to an eye of the user by the at least one light source; and a power supply unit for supplying power to the control unit and/or optical system. The light stimulation pulses activate the pupillary light reflex and one or more reflexes selected from: blink reflex; corneal reflex; menace reflex; and lacrimal reflex. When said device is in operation mode a light intensity gradient between the light pulses emitted by the at least one light source and the light around the eye is maintained at least 2 lumens, and wherein the light stimulation pulses induce blinking of the eye of the user.

In addition, in an alternative embodiment of the invention, the kit for stimulating the lacrimal gland and/or meibomian gland of an eye of a user includes a device for stimulating the lacrimal gland and/or meibomian gland of an eye of a user which is structured as a headset configured to interconnect with and accommodate a mobile phone. In addition, this kit further includes an access code to a service provider. In operation, the service provider operates the mobile phone to emit light stimulation pulses on the retina of the user to activate the pupillary light reflex and one or more reflexes selected from: blink reflex; corneal reflex; menace reflex; and lacrimal reflex. When the mobile phone is in operation mode a light intensity gradient between the light pulses emitted by the at least one light source and the light around the eye is maintained at least 2 lumens, and wherein the light stimulation pulses induce blinking of the eye of the user. The service provider may provide an App for the mobile phone or operate a program via a website.

An aspect of the invention, pertains to a method for stimulating dry eyes by emitting light on the retina, the method comprising the steps of: applying a device for stimulating the lacrimal gland and/or meibomian gland of an eye of a user in the vicinity of a facial region of an eye of a user, said device comprises: a control unit; an optical system connected to said control unit and arranged in the viewing direction of the user, said optical system includes at least one light source, and is configured for providing light stimulation pulses to an eye of the user; and a power supply unit for supplying power to said control unit and/or said optical system, generating light pulses by said at least one light source and emitting said pulses towards the eye of said user; emitting light on the retina; activating the pupillary light reflex and one or more reflexes selected from: blink reflex, corneal reflex, menace reflex, and lacrimal reflex; and inducing blinking of the eye of said user, wherein when said device is in operation mode a light intensity gradient between the light pulses emitted by said at least one light source and the light around the eye is maintained at least 2 lumens, and wherein said light stimulation pulses induce blinking of the eye of said user. In some embodiments, the method includes a step of generating light stimulation pulses in a random pattern in order to prevent the development of endurance of the eye. Specifically, the light source generates light stimulation pulses in a random pattern that surprises the user. In one or more embodiments, the optical system further comprises lens, adjustable lens and/or lens adjusting mechanism.

BRIEF DESCRIPTION OF THE DRAWINGS

Some embodiments of the invention are herein described, by way of example only, with reference to the accompanying drawings. Other devices, methods, features, and advantages of the present invention will be apparent to one skilled in the art upon examination of the following detailed description. Component parts shown in the drawings are not necessarily to scale, and may be exaggerated to better illustrate the important features of the present invention.

FIG. 4A is a view of the inside panel. FIG. 4B shows section A-A of the device shown in FIG. 4A. FIG. 4C shows the rotating element 402 of FIG. 4A.

DESCRIPTION OF THE EMBODIMENTS

Figure 1A:
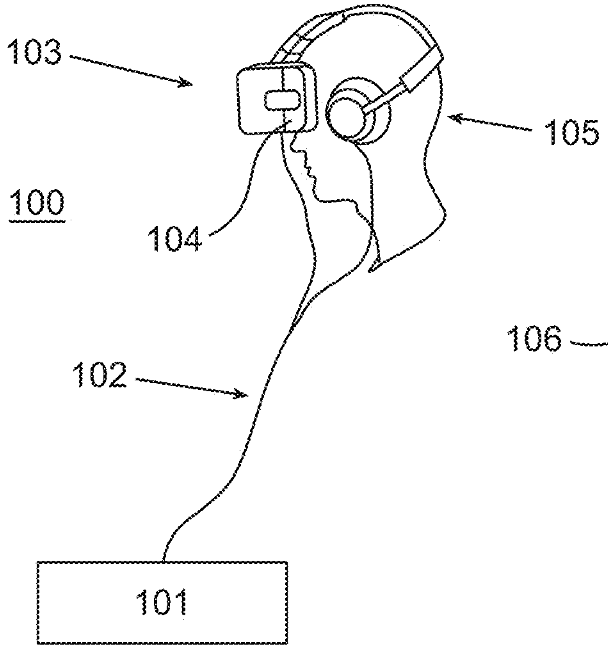
FIG. 1A is a side perspective view of a user wearing a device for stimulating the lacrimal gland and/or meibomian gland and the retina, generally referenced 100, constructed and operative in accordance with a preferred embodiment of the disclosed invention.

The following disclosure provides different embodiments or examples. Specific examples of components and arrangements are illustrated in the drawings and described below to simplify the present disclosure and for ease of understanding. These are, of course, merely examples and are not intended to be limiting. Thus, the invention is not limited to the specifically described products and methods and may be adapted to various applications without departing from the overall scope of the invention. In addition, the present disclosure may repeat reference numerals and/or letters in the various examples. This repetition is for the purpose of simplicity and clarity and does not in itself dictate a relationship between the various embodiments and/or configurations discussed.

The disclosure below presents embodiments of a novel device designed to stimulate tear secretion without direct physical contact with the eye itself, the skin in the vicinity of the eye or the eyelid. The device emits stimulation pulses towards the eye and thereby activates the pupillary light reflex and one or more reflexes selected from: blink reflex; corneal reflex; menace reflex and lacrimal reflex, whereas such activation induces tear secretion.

A reflex is an automatic action of the body in response to a stimulus. The anatomical pathway of a reflex consists of an afferent (or sensory) nerve, usually one or more interneurons within the central nervous system, and an efferent (motor, secretory, or secreto-motor) nerve. The pupillary light reflex is a well-known reflex. If a light is flashed near one eye, the pupils of both eyes contract. Light is the stimulus; impulses reach the brain via the optic nerve; and the response is conveyed to the pupillary musculature by autonomic nerves that supply the eye. The pupillary light reflex is a response to light that is modulated by visual awareness. Thus, it is important to enhance the efficacy of the indirect light treatment as presented in this disclosure. The pupillary light reflex controls the amount of light entering into the eye therefore in light pulses the importance of activating this reflex is laying on the fact that although blinking reflex is activated by the light the pupillary light reflex is important to prevent any potential damage to the eye retina when the device is activated.

Another reflex involving the eye is the lacrimal reflex. When something irritates the conjunctiva or cornea of the eye, the lacrimal reflex causes nerve impulses to pass along the fifth cranial nerve (trigeminal) and reach the midbrain. The efferent limb of this reflex arc is autonomic and mainly parasympathetic. These nerve fibers stimulate the lacrimal glands of the orbit, causing the outpouring of tears.

The eye blink reflex is elicited by an external stimulus such as a loud noise or a flash of a light or by predefined scenes or a tap on the forehead or by “irritating” the eyelash directly or indirectly.

The menace response is a blink reflex that occurs in response to the rapid approach of an object. The menace reflex comprises blinking of the eyelids, in order to protect the eyes from potential damage. Potential damage may be either actual i.e., potential movement of an element towards the eye, or virtual. When the human brain interprets a visual effect as a potential real threat to the eye, it responds in the same way even when there is no real threat. For example, a series of frames creating video for example a punch toward the system user, or car chase in which car seems going out of the device toward the user face may result the menace reflex although no actual contact between the virtual object and the eye are created.

The corneal reflex causes both eyes to blink in response to tactile stimulation of the cornea. As the cornea is the first substance irritants or foreign objects will touch when they come in contact with the eye. Contact with the cornea initiates the corneal reflex and tear production. The reflex activates when a sensory stimulus contacts either free nerve endings or mechanoreceptors within the epithelium of the cornea.

When activated, any one of the-above mentioned reflexes or a combination thereof stimulates the lacrimal gland and/or meibomian gland to output tears. Moreover, any combination of the blink, corneal, menace and lacrimal reflexes invokes a stronger blinking compared to a voluntary blink alone. Such a strong response may ease the dry eye symptoms of both the lacrimal and the meibomian glands.

To sum the above, the pulses emitted from the device of the present invention trigger neural signals through two separate anatomic pathways:

1. Optic tract fibers that terminate at the pretectal nucleus in the midbrain.
2. Autonomic and mainly parasympathetic neural pathways.

Furthermore, activation of sensory nerves in the corneal and conjunctival epithelia and stimulation of corneal sensory nerves cause fluid secretions and vasodilation in the lacrimal gland. The stimulation of corneal sensory nerves stimulates the lacrimal gland by a trigeminal-parasympathetic reflex.

The disclosed embodiments of the device provide a non-contact eyelid or orbital region treatment of DED. The stimulation pulses emitted towards the open or closed eye activate a sequence of eye blinks which in turn re-activate the lacrimal gland and optionally the meibomian gland leading to tear generation and self-restoration of the tear mechanism. In particular, use of the device of the invention is advantageous in cases where blinking reflex is weak due to environmental reasons, such as long exposure to computer screens at work. During the operation of the device, the eye may be open or closed, depends on the intensity of the pulse emitted from the at least one light source and the physical condition of the eye. The activation of these reflexes can be simultaneous or one after the other. A stimulation therapy which combines specific patterns and stimuli combinations can also be utilized for certain disorders. The retina contains molecules that undergo a chemical change upon absorbing light. For example, Retinol can be converted to retinal, and retinal is a chemical necessary for rhodopsin which enables night vision. As light enters the eye, the molecules may undergo an isomerization, or a change in their molecular arrangement. The new molecular form may not fit as well into the protein, and so a series of geometry changes in the protein begins. (Chemistry LibreTexts. 2016. Chemistry of vision. [online] Available at: <https://chem.libretexts.org/Bookshelves/Biological_Chemistry/Supplemental_Modules_(Biological_Chemistry)/Photoreceptors/Chemistry_of_Vision>).

The device of the invention activates the blink reflex to create an excessive tear production by the lacrimal gland and to change the composition of the tear film proteins hence affecting the biochemical processes in the eye and the eyelid. Among proteins within the tear film, growth factors, other proteins and vitamins such as vitamin A are playing a crucial role in controlling the process of dry eyes.

Definitions: As used herein the term "headpiece" and its derivatives refers to any of the following non-limiting examples: a headset, headphones, eye glasses, sun glasses or any other apparatus that can be worn on the head of the user and that to which can be coupled the device of the present invention.

The term "user" and its derivatives will be used herein to indicate any person or animal benefiting from lacrimal gland and/or meibomian gland stimulation.

The term "eye" will be used herein to indicate one eye of a user or both eyes of a user.

As used herein the term "virtual reality headset" is interchangeable with the term "VR headset" and refers to a smart headset unit. In addition, this term: "virtual reality headset" includes a virtual reality (VR) headset, an augmented reality (AR) headset, a mixed reality (MR) headset, or any other smart headset unit which can be placed on a face of the user.

As used herein the term "stimulation pulses" and its derivatives includes light pulses, sound pulses, vibration pulses, eyelash disturbance, air flow or any combination thereof that activates one or more reflexes selected from: blink, corneal, menace, lacrimal or pupillary light reflexes.

As used herein the term "stimulating the lacrimal gland and/or meibomian gland" refers to stimulation of the lacrimal gland only, stimulation of both lacrimal and meibomian glands and stimulation of only the meibomian gland when it is activated in connection with stimulation of the lacrimal gland. Preferable meaning is stimulating the lacrimal gland and optionally the meibomian gland.

Reference is now made to FIG. 1A, which illustrates a side perspective view of a user wearing a device for stimulating the lacrimal gland and/or meibomian gland, generally referenced 100, constructed and operative in accordance with a preferred embodiment of the disclosed invention. Device 100 is constructed as a headpiece that can be worn on the head of a user. Device 100 includes control unit 101 which is connected to an optical system 103 via a wire 102. Optionally, control unit 101 may include a wireless connection to optical system 103. The control unit 101 is programmed to actuate the optical system and any other means for providing stimulation pulses that are integrated in the device. Optical system 103 is configured for providing stimulation pulses to an eye of the user by at least one light source (not shown). Optical system 103 is arranged in the viewing direction of the user. Optical system 103 may further comprise lens, adjustable lens and/or lens adjusting mechanism (not shown). In other embodiments, the light source provides light stimulation pulses in a random pattern. The light source may include a series of LEDs that may emit light all together or emit light one after the other in many configurations and patterns, as desired in order to obtain a result.

The optical system 103 further includes a power supply unit so that it can be self-energized. The power supply may be a battery, a radiated power source or a solar panel. Alternatively, optical system 103 may be powered from the control unit. In the embodiment shown in FIG. 1A, the power supply unit is integrated with control unit 101. However, it should be noted that, the power supply unit may be integrated with or arranged within the optical system, as well. In other embodiments, the device may be constructed to connect an external power supply unit or even plug to domestic power via a wire/adapter.

Figure 1B:
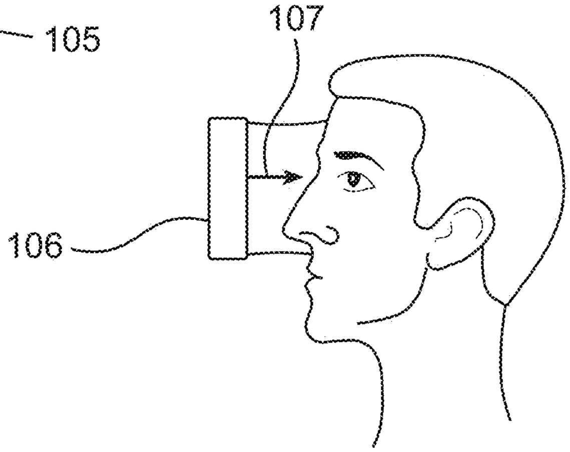
FIG. 1B is a side view illustration of optical system 103 (shown in FIG. 1A).

FIG. 1B, is a side view illustration of optical system 103 (shown in FIG. 1A) depicting the arrangement of the light panel 106 and the light direction 107 towards the face of the user. It should be noted that the light source does not contact the skin or eyelids. The light panel 106 may have at least one light source for emitting light to any eye of the user. However, some embodiments of the invention may include two or more light emitting sources, as required. The light pulses are emitted at a random sequence. In some embodiments, the light source provides light stimulation pulses in a random pattern and sequence in order to prevent the development of endurance of the eye. In other words, the light source generates light stimulation pulses in a random pattern that surprises the user. In one or more embodiments, the optical system further comprises lens, adjustable lens and/or lens adjusting mechanism that can be adjusted horizontally, vertically, or a combination thereof to fit a specific face structure.

The light source is limited to the visible spectrum (wavelength 350-750 nm). It should be noted that an embodiment of the device may use wavelength limited to the visible light only. This embodiment may include dedicated filters and other means for reducing IR emission. The maximal light intensity depends on the light source, pulse sequence and other factors as describe by Boyuan Yana et. al., "Maintaining ocular safety with light exposure, focusing on devices for optogenetic stimulation", Vision Res. 2016 April; 121: 57-71. doi:10.1016/j.visres.2016.01.006. In addition, the American National Standards Institute (ANSI) Z136.1-2000 Standard provides details on the amount of energy for ophthalmic device. For example, some embodiments of the device of the invention may emit light at an intensity between 5 lumens to 2500 lumens, measured at a distance of 1 cm from the light source. It should be noted that the device may include a pulse light source in a close chamber for various sizes of the device. The light source pulse maintains the requirement that the light intensity gradient between the light source and the environment shall be at least 2 lumens.

Furthermore, the control unit may be programmed to operate the optical system in a predetermined sequence according to a required treatment. The control unit may be further provided with a user-friendly app that enables a user to select the most suitable treatment for his/her eye condition. Such app can be a computer program or software application designed to run on a mobile device such as a phone, tablet, or smart watch. Optionally, the control unit includes an algorithm that is programmed to allow the optical system to generate a sequence of pulses at period varies between 0.1 msec (millisecond) to 10 minutes. The number of pulses per session shall vary between 1 to 1,000 pulses. Treatment regimen shall include between 1 to 20 treatment sessions every 1 to 100 days.

Referring back to FIG. 1A, a shading element 104 is positioned between the light source or light source panel and the eye (or eyes) and constructed to maintain a light intensity gradient between the light source and the environment to at least 2 lumens. Alternatively, the device may be operated in a dark environment leading to the same anticipated light gradient between the light source and the environment. In the embodiment shown in FIG. 1A control unit 101 is also connected by wire to earphones 105. It should be noted that, the shading element may contact the face for shading purposes only, i.e. to provide sufficiently dark environment required for triggering blinking. The shading element is therefore, not an active element in stimulating any of the lacrimal, blink, corneal, menace or pupillary light reflexes. The shading element is an optional element.

Further embodiment of device 100 may be designed for coupling with a conventional eye or sun glasses. An alternative embodiment of device 100 may be constructed to couple with conventional headphones. Yet, additional embodiment of device 100 may be configured to interconnect with a virtual reality (VR) headset or augmented reality (AR) headset or mixed reality (MR) headset, or any other smart headset unit which can be placed on a face of the user. Furthermore, device 100 may be powered from the control unit 101, the optical system 103 or constructed to be self-energized by any means of power supply such as battery, radiated power source, solar panel etc.

When mounted on the head of the user, device 100 can optionally be used with an external control unit, such as a personal computer, laptop, tablet, cell phone and any other microprocessor-controlled unit that is capable of controlling the optical system mounted on the user's head. In an alternative embodiment, the control unit is arranged in the device. Yet in additional embodiments of the invention the control unit includes two elements one is external and the other is installed inside the device. In these embodiments, both elements are wireless interconnected.

Control unit 101 is programmed to activate optical system 103 to generate stimulation pulses in order to control the blinking, and/or pupil, and/or lacrimal reflex of the user eyes without any contact between the light emitted from light source 107 mounted on a panel 106 (FIG. 1B). The eye reflexes may be activated not only by means of indirect light pulses but also with any one of the optional additional means of sound pulses, vibration pulses, eyelash disturbance, or any combination thereof. The sound pulses may be activated in parallel to the light pulses or separately. Sound pulses may produce a secondary menace reflex. Sound pulses characteristics have similar characteristic to the light pulses.

Optionally, light and sound pulses may be configurated to describe a realistic scenario such as short video of car progressing toward the eyes of the user in order to activate the eye menace reflex as a result of user's response to a virtual or augmented threat to the eye. Such may be combined with sound and optionally also by vibrations, which together create a situation perceived by the user as realistic scenario for activating the menace or panic reflex of the eye resulting fast blinking of the eyelids.

Control unit 101 may be programmed to activate optical system 103 to generate a sequence of light pulses at a frequency of 10 pulse per seconds up to 1 pulse every 5 minutes, in the visible range. Pulse duration may vary between 0.1 millisecond to 20 seconds, in order to initiate the photo-lacrimal reflex. While the retina is stimulated by an excess of light, it produces a lacrimal secretion through the afferent optic and efferent lacrimal pathways. It should be noted that optical system 103 is not connected to the eye, eyelid or to the face.

The device may generate sound between 5 Hz to 20 Khz complying with limits presented on ISO Standard 1999. In some embodiments, the device generates sound between 5 Hz to 10 Khz. The EU has published a scientific committee report on the Potential health risks of exposure to noise from personal music players and mobile phones including a music playing function. The design of the device will comply with the requirements presented in this document. The sound pressure values may vary between 1 dB to 135 dB. Sound pulses may vary between 0.01 second to 5 minutes.

Figure 2A:
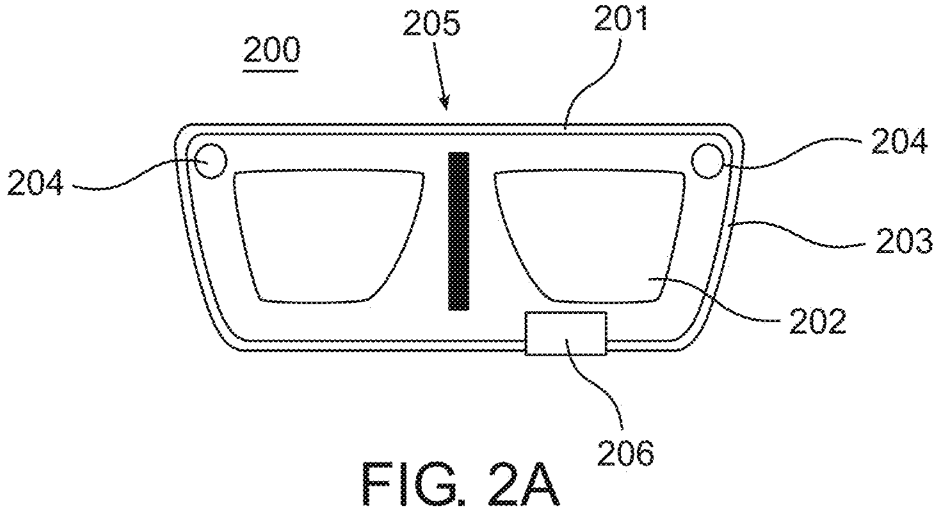
FIG. 2A. illustrates schematically the inside panel of an additional embodiment of a device according to the invention, as viewed from the eye of the user.

Referring now to FIG. 2A, which illustrates schematically the inside panel of an additional embodiment of a device according to the invention, as viewed from the eye of the user, generally referenced 200. Mounting structure 201 serves as a scaffold or panel for optical system 200 which includes light source items 202. Mounting structure 201 may be made of a rigid material such as metal or flexible material such polymer or elastomer, for example, rubber, silicon rubber, EPDM, PET, nitril, polyacrylic rubber, fluoro-rubber, thermoplastic elastomer, polysulfide. Mounting structure 201 may have the shape of an ordinary eyeglasses as depicted in FIG. 2A. Alternatively, mounting structure 201 may be constructed as a solid spherical shape to prevent any light penetration from the front side of the device.

Light source 202 is attached to mounting panel 201 and connected to a power supply unit 206 which is an internal power pack (for example, batteries rechargeable or disposable) power source may be coupled to an external power source. Light source 202 may comprise, for example, a series of LEDs, a light bulb, electroluminescent display (ELD), LCD display, OLED display or any combination thereof. Light source 202 may be configured to emit light pulses, light frames or short video scenarios or scripts for activation of an eye to induce blink reflex and/or pupillary light reflex and/or lacrimal reflex. A combination of different types of reflexes is required to activate the lacrimal gland and optionally the meibomian gland. When light is emitted directly to the retina and the light gradient between the projected light and the light level of the surrounding area is maintained at 2 lumens, the pupil reflex (pupillary light reflex) is activated.

The system may include at least one light source that emit light. In some embodiments, the device includes between 1-10 light sources. However, the number of light sources may vary and depends on different parameters of the device and the light source characteristics. Light shading element 203 is positioned such that it can cover the whole volume between the mounting structure 201 and the user's face or provide a partial coverage varying between 5-100% of the mounting structure's outer perimeter. Light shading element 203 can be made of a fabric, elastomer, polymer, or any other combination thereof.

Before operating the device, the eye is exposed to a dark environment, due to the use of light shading element 203. Upon operation, when light source 202 emits light and activates one or more of the above-mentioned reflexes, the eye blinks due to a rapid exposure of the eye retina to a light in the visible range. Each light source can be activated alone or simultaneously with at least another light source. The sequence of light pulses is random and unexpected. It may be in different patterns, from different angles and directions. Light pulses may be programmed to activate blinking on each eye separately in response to blink reflex, corneal reflex, menace reflex, lacrimal reflex and/or pupillary light reflex, although activation of the said reflexes in one eye may result the activation of the reflexes in both eyes simultaneously. In order to be able to activate each eye separately, an optional partition 205 positioned between the light sources (optionally attached to mounting structure 201) to provide better separation between the light sources.

An embodiment of the device may include a feedback element such as a camera 204. Camera 204 is provided for allowing close loop control on the activation of the different eye reflexes and to enable modifying the light pulses characteristics such as light intensity, pulse duration, pulse sequence according to the requirements of the user. The camera may also provide the option to better monitor and control the sound and vibration characteristics used for inducing the menace reflex solely or in parallel to the light pulse sequences. Furthermore, in another embodiment of the invention, the camera is interconnected with the light source and the control unit for evaluating the tear breakup time (TBUT) by measuring the time elapse from blinking until tear film breaks. The measurements can be presented in seconds or by any other indicative form. The system may be used before the treatment, during treatment and/or after the treatment for evaluation. The evaluation may provide indication of the progress made by the user. An alternative embodiment of the device may include a feedback element such as a camera or photo sensor that can for example evaluated the blinking effect as a function of the reflex activation mechanism (light, sound, irritation, etc.) and can modify the activation sequence, intensity, period, frequency and light and/or sound combined with "irritation algorithm for example changing the VR scenario (i.e., from car race to snow collapse).

Figure 2B:
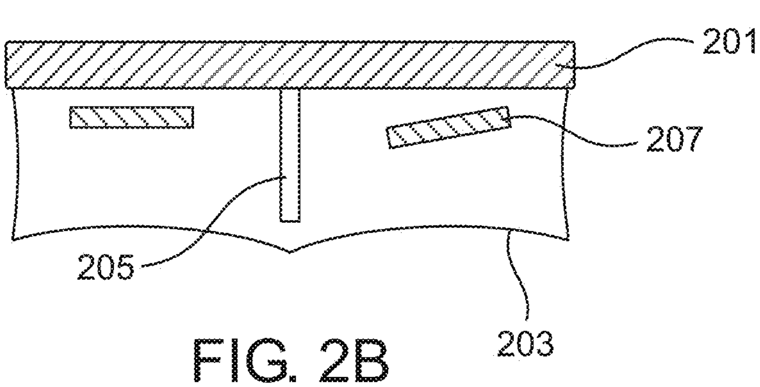
FIG. 2B. is a cross sectional view of the embodiment of the device shown in FIG. 2A when viewed from above.

In some embodiments, the device may contain one, two or up to 10 cameras allowing recording the correlation between the reflex's activation methos, i.e., light, sound, vibration, eye lashes irritation as later described and the eye pupil, blinking and lacrimal reflex. The reflex reaction shall be analyzed using deep learning algorithms aiming to analyze the eye blinking characteristics. The deep learning algorithm allows determine the blinking characteristics such as: blinking speed, pupil dimensions in correlation with the different reflexes' activation. In addition, the data may be integrated into AI algorithm to allow teaching the system to adjust the different pulses sequences to fit a specific user based on his unique behavior following the reflex activation element as described herein. FIG. 2B is a cross sectional view of the embodiment of the device shown in FIG. 2A when viewed from above. The light source that may be aligned with the mounting structure 201 (FIG. 1A) may also be angled 207 as shown in FIG. 2B. The angle may vary between 0-45 degrees.

Figure 3:
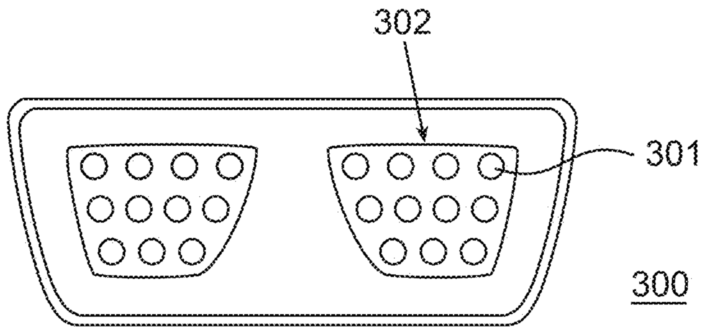
FIG. 3 illustrates schematically the inside panel of an additional embodiment of a device according to the invention, as viewed from the eye of the user.

FIG. 3 illustrates schematically the inside panel of an additional embodiment of a device according to invention, as viewed from the eye of the user, generally referenced 300. FIG. 3 depicts an exemplary system configuration of the light source. Light source 301, in the instant embodiment, includes a series of light emitting elements that emit light in the visible range at a light intensity up to 2500 lumen. In some cases, light intensity may be a function of the light pulse. For example, for a very rapid pulse ranging between 0.1 millisecond to 100.0 second, the light pulse may reach the highest value, whereas in long pulses the light intensity may be reduced to 100 up to 400 lumen. As stated above, light source 301 may include a series of LEDs, a light bulb, electroluminescent display (ELD), LCD display, OLED display or any combination thereof. The array of light emitting elements 302 may include from a single light source up to 10,000 individual elements arranged in rows and columns in a single or multiple arrays of light sources. The number of rows and columns may vary between 1 to 5000. Light source size can vary for example, between 0.5 $cm^2$ to 15 cm (in length) for each light source array 302. These size dimensions are, of course, merely examples and are not intended to be limiting. The light source may include a series of LEDs that may emit light all together or emit light one after the other in many configurations and patterns, as desired in order to obtain a result.

Light source 301 may emit light in all the visible range. Furthermore, Light source 301 may emit a single color i.e., white, blue, green, red or any combination of the RGB (red, green, blue), or any color defined by Panton color scheme light composition. The light source 301 refresh time for generating a new pulse of light vary between 1 millisecond to 2 minutes.

Figure 4A:
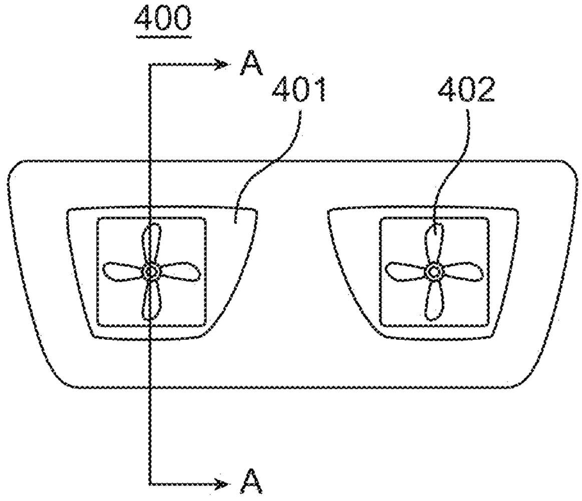
FIGS. 4A-4C. illustrate a concept view of an exemplary device which includes rotating element according to one aspect of the present invention.
Figure 4B:
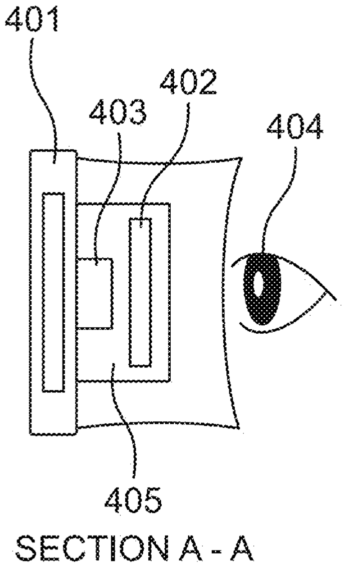
Figure 4C:
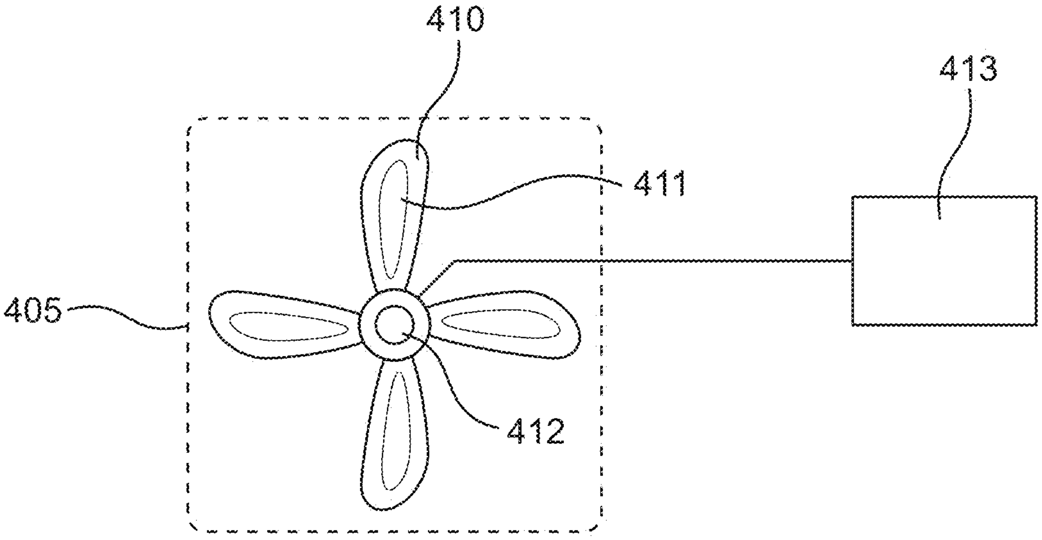

Certain embodiments of the device may include arrays of light emitting elements that can project light towards the eye of the user according to a predesigned pattern. Exemplary patterns may include horizontal paths, vertical paths, circular paths etc. The user follows the light path and by doing so exercise the eyes muscles. An additional embodiment of the device is an eye training application. The device's light source can be configured to train a controlled eye movement in order to train eye muscles. One example is a light source configured in rows and columns or at a random angle. The operator may select a row or column or a specific LED or light source and then run an exercise. A similar solution can be obtained using a raster-type display consisting of pixels. In order to create a controlled eye movement to train the eye muscles, the operator can turn on and off a specific light raw, column, or angle. The lighting sequence can include only one side light source (right or left) and/or two sides simultaneously. Another option is a single light or an array of LED or pixels. The light sequence can last between 0.1-300 seconds when a light source is on. The treatment sequence can take between 10-2,000 seconds. The intervals between light source on and off can take between 0.1 to 300 seconds. FIGS. 4A-4C depict a concept view of an exemplary device which includes rotating element according to one aspect of the present invention, generally referenced 400. FIG. 4A is a view of the inside panel. FIG. 4B shows section A-A of the device shown in FIG. 4A. FIG. 4C shows the rotating element 402 of FIG. 4A. This embodiment activates the pupil, blink, corneal, lacrimal and menace reflex (each or any combination thereof). It should be understood that the rotating element can be used in combination with any other embodiment of the invention.

FIG. 4A depicts light source 401 and rotating element 402. As can be seen from FIG. 4B, rotating element 402 is a disc which is placed between light source 401 and the eye of the user 404. Optionally, rotating element 402 can have any one of the following shapes: circular, ellipse, irregular shape, rectangular, disc with irregular shape extensions. One example, a fan 410 as illustrated in FIG. 4C. Rotating element 402 may include series of lumens 411 (light sources) allowing passage of light through the rotating element. The number of lumens 411 per rotating element can vary between 1 to 10,000,000 wherein the lumens can be arranged randomly on the rotating element. Rotating element 402 rotates around a central shaft 412. The rotation rate can be a single rotation or a sequence of rotations at a frequency between 0.001-100 Hz.

In one configuration of the rotating element, the rotating element may take the form of fan blades allowing in addition to optical effect, delivering of air at 0.1-50 cfm in a continuous mode or in pulses lasting between 1 to 1000 seconds during treatment. The air flow may activate the corneal reflex by creating air flow over the eyelash. The rotating discs may be activated simultaneously or separately.

With reference to FIG. 4B, it can be seen that the rotating element 402 is positioned close to the eye, whereas electric motor 403 is positioned between rotating element 402 and light source 401. The rotation of the rotating element may be conducted by an integral or external electric motor 403 (DC, brushless, DC brushless, AC motor) or solenoid. In addition, linear motor or optional solenoid 413 (FIG. 4C) instead of an electric motor 403 may be used as actuator to generate rotating element movement. The range of motion can be limited to a range of 5° up to full rotation. The light pulse sequences may be synchronized to allow optimal activation of the eye reflexes based on actual dry eye relief results and or based on AI data collection and analysis. The fan like element may include an enclosure 405 (FIG. 4C).

FIG. 4B shows the orientation of the fan and a schematic assembly of the fan and the light source and the eye. In case a fan is installed the objective of the fan is to combine light pulse with air flow on the eyelash at airflow range between 0.01 cfm to 50 cfm. In case two fans are installed, each fan can be activated in a different air flow. In addition, each fan can work independently from the other. In some cases, only one fan is operated while the other is off. Fans can work continuously or in pulses generating air flow pulses.

Figure 5:
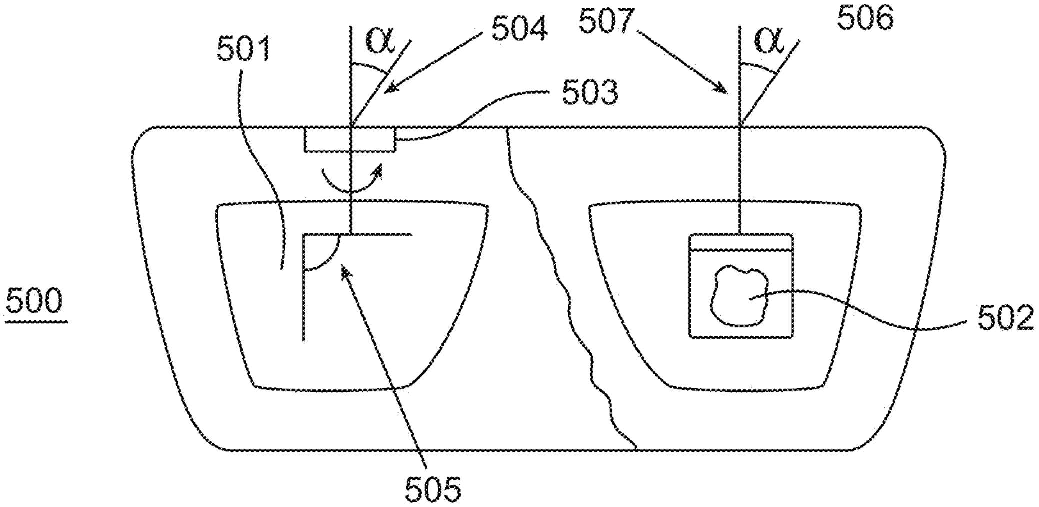
FIG. 5. illustrate schematically an alternative embodiment to the embodiment shown in FIGS. 4A, according to one aspect of the present invention.

An alternative embodiment to the embodiment shown in FIGS. 4A-4C is illustrated in FIG. 5, the device 500 generally includes rotating element 501 made of rigid or flexible material which can be formed in various shapes as described in connection with FIGS. 4A-4C. In the instant embodiment rotating element 501 is a disc with irregular shape 505. In the instant embodiment, as well as in the embodiment depicted in FIGS. 4A-4C, rotating element 402 is located between the light source 401 and the eye, and includes as shown in FIG. 5 series of lumens 502 allowing passage of light through the rotating element. The number of lumens 502 per rotating element can vary between 1 to 100 and may be arranged randomly on the rotating element. The rotating element shall rotate around a central shaft 507 (second rotation axis). Rotating element 501 may induce blinking, lacrimal or menace reflex (together or any combination of the reflex or each reflex separately) due to element rotation or combination of element rotation and light activating the photo lacrimal reflex. The rotation rate can be a single rotation or a sequence of rotations at a frequency between 0.1-100 Hz. The rotating element may be oriented in spatial angles (506, 504). The rotation axis shall be motored by an electrical motor or solenoid 503.

Figure 6:
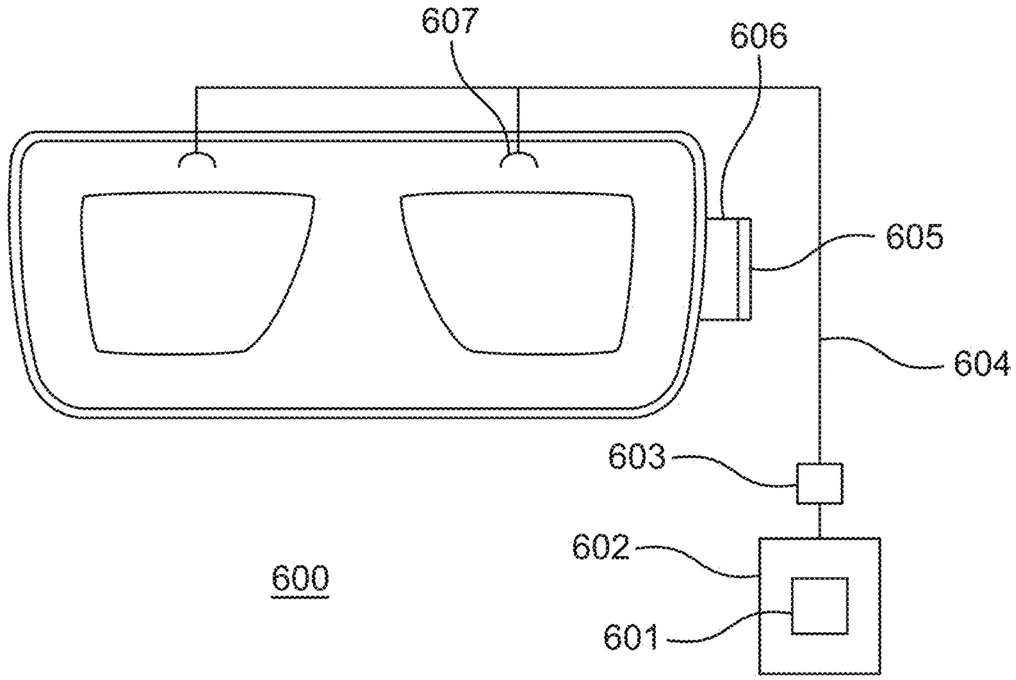
FIG. 6. illustrate schematically an embodiment of the invention in which air flow and/or water drops are used, according to one aspect of the present invention.

FIG. 6 depicts an embodiment of the invention in which air flow and/or water drops are used for stimulating the pupillary light reflex and/or blink reflex and/or lacrimal reflex and/or menace reflex or any combination of these reflexes. For liquid spray system: device 600 consists a liquid reservoir 601 enclosed in a housing 602. The liquid in the reservoir may be sterile or non-sterile and is kept at a temperature between 0° C. to 60° C., preferably at room temperature. For example, the liquid is water or saline. A pump or piston 603 is connected to reservoir 601 and generates sufficient pressure required to deliver the liquid from reservoir 601 via tube 604 to nozzles 607 positioned inside device 600. Device 600 may include 1, 2, 3 . . . 6 nozzles 607 that can generate tiny liquid drops and spritz a small amount of liquid within the device in vicinity of the eye of the user. The blink reflex and lacrimal reflex are activated when the liquid drops are reaching the eyelid or the cornea during distribution. the liquid reservoir 601 and the pump 603 can be integrated together into housing 602. Alternatively, device 600 can be adapted to contain liquid reservoir 601 and pump 603 in a special compartment integrated with its mounting structure, for example mounting structure such as 106 (FIG. 1) or 201 (FIG. 2A). An optional air or other gas such as nitrogen, $CO_2$, argon, circulating system that can be added to the embodiment depicted in connection with FIG. 6 consists of an electric fan or blower 606 installed on the device walls (external or internal and on each wall i.e., side, top, bottom). An air filter 605 may be installed as well to prevent particles entering into the device internal volume resulting eye irritation. The ventilation system provides air flow inside the device and thereby activates the blink and lacrimal reflex. The fan or blower may be connected to nozzles 607 inside the device for homogenous air flow inside the device.

Figure 7:
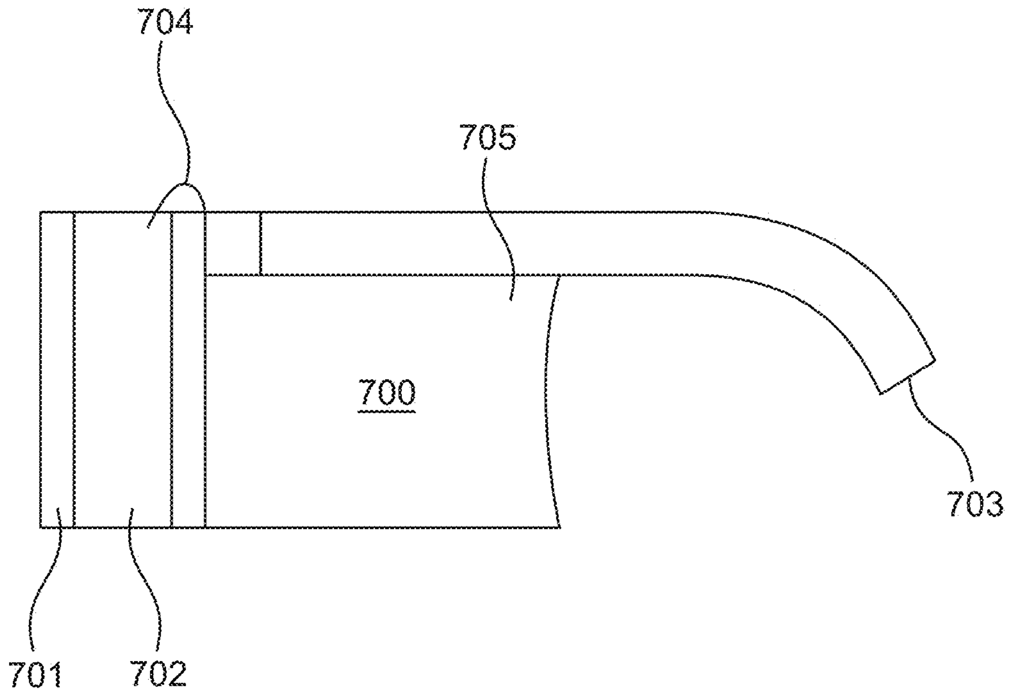
FIG. 7. illustrate schematically a general configuration of an exemplary embodiment of the invention when assembled on eyeglasses.

With reference now to FIG. 7, which depicts a general configuration of an exemplary embodiment of the invention when assembled on eyeglasses generally referenced 700. Device 700 includes coupling means 704 for releasably coupling the device with a conventional eye or sun glasses or googles. Optionally, coupling means 704 may also be configured to couple with a headset or any other headpiece. Light emitting element 701 is installed on the frontside of the device over the goggles front frame 702. The rear goggles element over the ears includes a sound emitting element 703. The light emitting part is rigidly connected to the goggles using a latch as coupling means 704 or any other fastener which provides a sufficiently tight and safe attachment. In alternative embodiments, coupling means 704 may be a magnetic set, pins and/or nose piece that allow height adjustments to accommodate different users. The device may include a shading element 705 similar to the one shown in FIG. 2A. It should be noted that all mechanical components described in the figures of the current invention may contact or may not contact the eye, eyelashes, and/or the eyelids.

Figure 8:
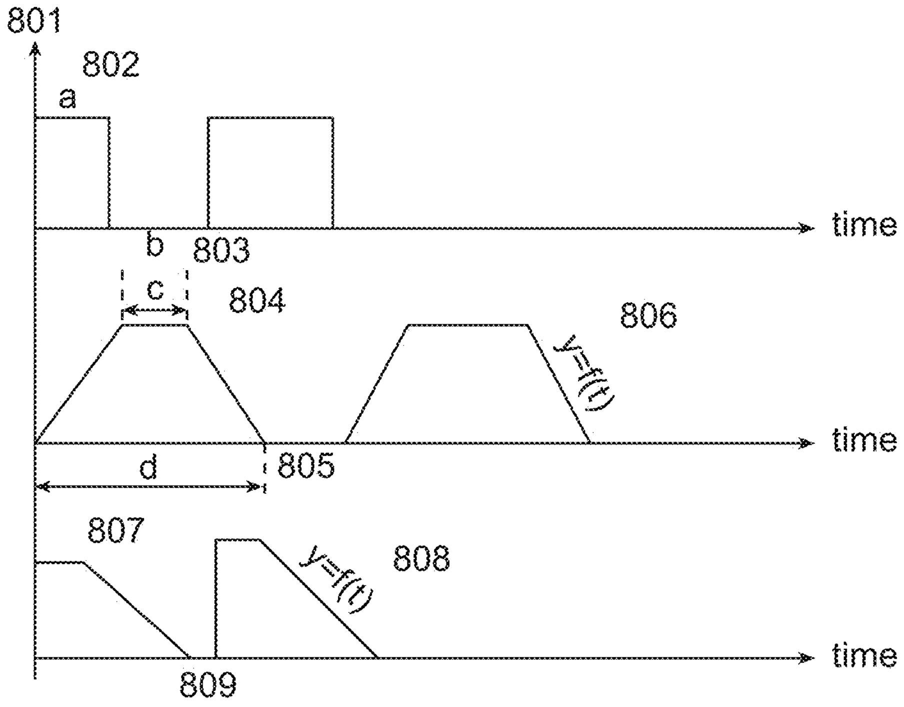
FIG. 8. illustrate the light system pulse characteristics of an exemplary optical system that may be used in conjunction with the device of the invention.

FIG. 8 illustrates the light system pulse characteristics of an exemplary optical system that may be used in conjunction with the device of the invention. Light intensity 801 as a function of time may have different pulse shapes. For example, a step function with pulse duration 802 and intensity a, which can vary between 1 millisecond to 5000 seconds and time interval between pulses b that can vary between 1 millisecond to 5000 seconds. The duration of the second pulse 803 can be similar to the first pulse or as shown a bit longer. The number of pulses per session can vary between 1 to 5000. An alternative pulse shape is trapezoid or trapezoid like shape where the light intensity vs. time take 806 is in the form of PL-f(t). The function can be linear, logarithmic, exponential, polynomic of up to 10th order. The total pulse duration 804 (D) may vary between 1 millisecond to 5000 seconds and time interval between pulses 805 may vary between 1 millisecond to 5000 seconds. The number of pulses per session can vary between 1 to 5000. An additional alternative is illustrated at the lower graph, in which the pulse shape is a Sawtooth wave or Sawtooth wave like shape 807 where the light intensity vs. time takes 808 is in the form of PL-f(t). The function can be linear, logarithmic, exponential, polynomic of up to 10th order. The total pulse duration 808 may vary between 1 millisecond to 5000 seconds and time interval between pulses 809 may vary between 1 millisecond to 5000 seconds. The number of pulses per session may vary between 1 to 5000. In some embodiments, the light source provides light stimulation pulses in a random pattern in order to prevent the development of endurance. For example, a combination of different pulse shapes and durations selected from a predetermined data set for a specific disorder and age. The light source generates light stimulation pulses in an unpredictable pattern that surprises the user. In one or more embodiments, the optical system further comprises lens, adjustable lens and/or lens adjusting mechanism.

Figure 9:
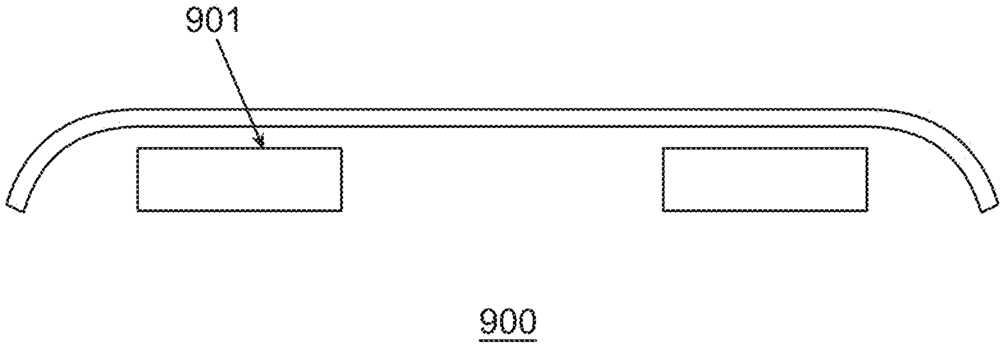
FIG. 9. illustrate schematically an embodiment of the invention that includes a vibration source operable by the control unit, according to one aspect of the present invention.

FIG. 9 is a schematic illustration of an embodiment of the invention that includes a vibration source operable by the control unit generally referenced 900. As shown, FIG. 9 depicts a piston 901 that is constructed to produce a combination of portion sound and vibration as a function of time. Piston 901 (mechanical, electrical, magnetic, pneumatic) may actuate different pulse shapes. Piston 901 may be open loop or closed loop controlled (not shown in the figure). For example, a step function with pulse duration 802 that may vary between 1 millisecond to 5000 seconds and time interval between pulses b that may vary between 1 millisecond to 5000 seconds. The number of pulses per session may also vary between 1 to 5000. The piston may be a solenoid, electric motor, pneumatic or hydraulic piston. The generated pulse can be hidden or can be exposed to the eye during activation.

Figure 10:
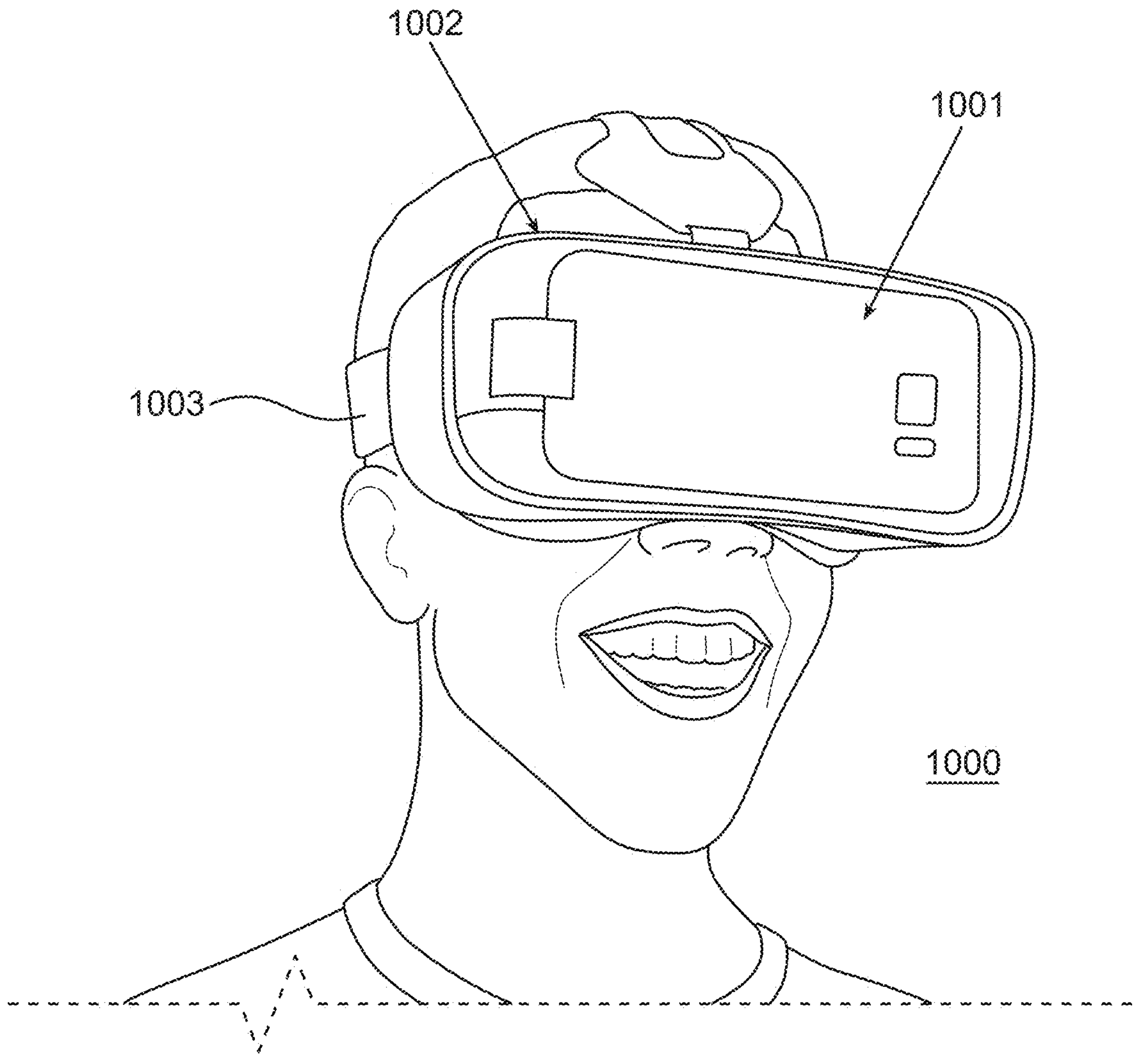
FIG. 10 is a front perspective view of a user wearing a device for stimulating the lacrimal gland and/or meibomian gland, generally referenced 1000, constructed and operative in accordance with a preferred embodiment of the disclosed invention.

FIG. 10 is a front perspective view of a user wearing a device for stimulating the lacrimal gland and/or meibomian gland, generally referenced 1000, constructed and operative in accordance with a preferred embodiment of the disclosed invention. Device 1000 comprises a headpiece or mounting structure 1002 with coupling means 1003 for releasably coupling a mobile phone 1001 with mounting structure 1002. Mobile phone 1001 includes a control unit, an optical system, a light source and a power supply unit. Mounting structure 1002 is configured to interconnect with mobile phone 1001. Furthermore, mounting structure 1002 is constructed to accommodate a mobile phone such that the display screen of the mobile phone is facing the user's eyes. In addition, the mobile phone uses a user-friendly app that enables a user to select the most suitable treatment for his/her eye condition. Such app can be a computer program or software application designed to run on a mobile device such as a cellphone, tablet, or smart watch. Further, while operation, the app can be accessed and controlled by the user, via a personal computer, another cellphone, tablet, or smart watch. The present invention, in some embodiments relates to kits for stimulating dry eyes. In some embodiments of the invention a kit for stimulating the lacrimal gland and/or meibomian gland of an eye of a user includes a device for stimulating the lacrimal gland and/or meibomian gland of an eye of a user and coupling means for releasably coupling the device with a conventional eye or sun glasses. In some embodiments, the device includes a control unit and an optical system connected to the control unit and arranged in the viewing direction of the user. The optical system includes at least one light source, and is configured for providing light stimulation pulses to an eye of the user by the at least one light source; and a power supply unit for supplying power to the control unit and/or optical system. The light stimulation pulses activate the pupillary light reflex and one or more reflexes selected from: blink reflex; corneal reflex; menace reflex; and lacrimal reflex. When said device is in operation mode a light intensity gradient between the light pulses emitted by the at least one light source and the light around the eye is maintained at least 2 lumens, and wherein the light stimulation pulses induce blinking of the eye of the user.

In addition, in an alternative embodiment of the invention, the kit for stimulating the lacrimal gland and/or meibomian gland of an eye of a user includes a device for stimulating the lacrimal gland and/or meibomian gland of an eye of a user which is structured as a headset configured to interconnect with and accommodate a mobile phone. In addition, this kit further includes an access code to a service provider. In operation, the service provider operates the mobile phone to emit light stimulation pulses on the retina of the user to activate the pupillary light reflex and one or more reflexes selected from: blink reflex; corneal reflex; menace reflex; and lacrimal reflex. When the mobile phone is in operation mode a light intensity gradient between the light pulses emitted by the at least one light source and the light around the eye is maintained at least 2 lumens, and wherein the light stimulation pulses induce blinking of the eye of the user.

Yet another alternative embodiment of the invention is a kit for stimulating the lacrimal gland and/or meibomian gland of an eye of a user that includes a mounting structure adapted to fit onto said user's face and constructed to accommodate a mobile phone; and an access code to a service provider. In operation the service provider operates the mobile phone to emit light stimulation pulses on the retina of the user to activate the pupillary light reflex and one or more reflexes selected from: blink reflex; corneal reflex; menace reflex; and lacrimal reflex. When the mobile phone is in operation mode a light intensity gradient between the light pulses emitted by the at least one light source and the light around the eye is maintained at least 2 lumens. The light stimulation pulses induce blinking of the eye of said user.

The present invention, in some embodiments relates to methods for stimulating dry eyes. In some embodiments of the invention, a device may be applied in the vicinity of a facial region of an eye of a user, for stimulating the lacrimal gland and/or meibomian gland of an eye of the user. The caregiver or doctor selects the treatment plan for a specific user via an App in the mobile phone or the computer. The treatment plan enables selection of preferably: the number of light pulses, range of wavelength band and time intervals between the stimulation light pulses. The method comprises applying a device for stimulating the lacrimal gland and/or meibomian gland of an eye of a user in the vicinity of a facial region of an eye of a user. When the device is in operation mode, it emits light on the retina. The emitted light activates changes in the tear chemical composition and induces severe meibum secretion. The device comprises: a control unit; an optical system connected to said control unit and arranged in the viewing direction of the user. The optical system includes at least one light source, and is configured for providing light stimulation pulses to an eye of the user. A power supply unit for supplying power to said control unit and/or said optical system is also provided. The method further includes the steps of generating light pulses by at least one light source and emitting said pulses towards the eye of said user; activating the pupillary light reflex and one or more reflexes selected from: blink reflex, corneal reflex, menace reflex, and lacrimal reflex; and inducing blinking of the eye of said user. Wherein when the device is in operation mode a light intensity gradient between the light pulses emitted by the at least one light source and the light around the eye is maintained at least 2 lumens. Furthermore, wherein said light stimulation pulses induce blinking of the eye of the user. The device operates without physical contact with the eyes or eyelids.

Yet, alternative embodiments of the invention relate to methods for stimulating the lacrimal gland and/or meibomian gland of an eye of a user. The method comprises applying light stimulation pulses in the vicinity of a facial region of an eye of a user by emitting light on the retina; activating the pupillary light reflex and one or more reflexes selected from: blink reflex; corneal reflex; menace reflex; and lacrimal reflex; activating changes in the tear chemical composition which induce sever meibum secretion. These steps are repeated as necessary to induce blinking of the eye of the user. The light intensity gradient between the light pulses emitted by the at least one light source and the light around the eye is maintained at least 2 lumens.

Figure 11:
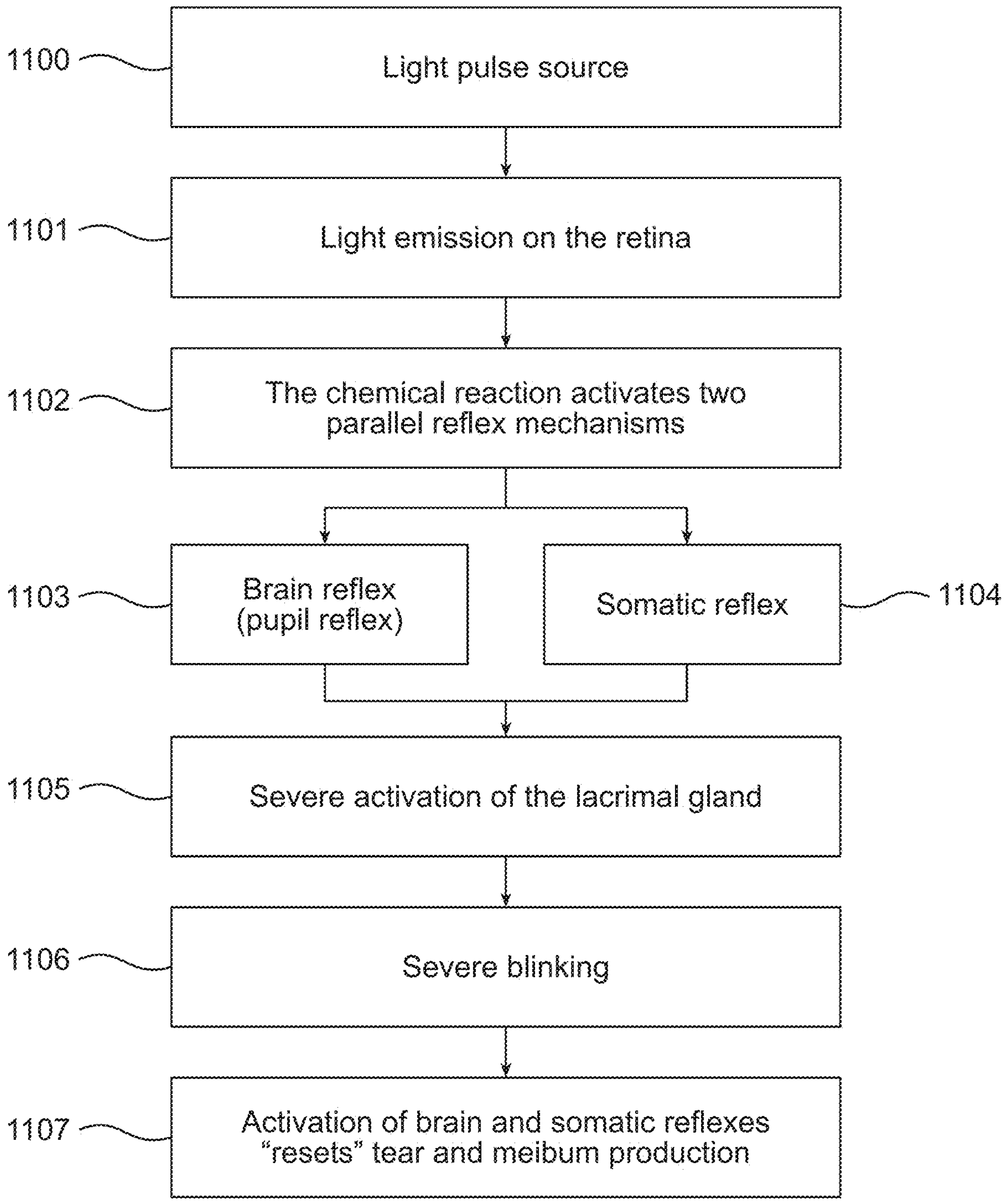
FIG. 11 provides a schematic flowchart that presents the therapeutic effect of light on dry eyes in accordance with a preferred embodiment of the disclosed invention.

FIG. 11 provides a schematic flowchart that presents the therapeutic effect of light on dry eyes in accordance with an embodiment of the disclosed invention. With reference to FIG. 11, light pulse source 1100, emits light on the retina and activates chemical reactions 1101. The chemical reactions activate two parallel reflex mechanisms 1102: Brain reflex 1103 which is activated by pupil reflex and Somatic reflex 1104. Both reflexes 1103 and 1104 cause severe activation of the lacrimal gland 1105 thereby producing excessive tears. Along with activation of the reflexes 1103 and 1104, severe blinking 1106 occurs. At the end of the process, activation of multiple brain somatic reflexes re-sets tears and meibum secretion 1107.

Some alternative methods may include any one of the following steps or any combination thereof: applying light at the visible spectrum of wavelength band of 350-750 nm; operating sound source alone or in combination with the emission of light; applying vibrations to the user; producing eyelash disturbance; activating a rotating element in the line of sight of the user; generating air flow towards the eyes of the user; spraying water drops towards the eyes of the user. In some embodiments, the method includes a step of generating light stimulation pulses in a random pattern in order to prevent the development of endurance of the eye. Specifically, the light source generates light stimulation pulses in a random pattern that surprises the user. In one or more embodiments, the optical system further comprises lens, adjustable lens and/or lens adjusting mechanism.

It will be appreciated by persons skilled in the art that the disclosed invention is not limited to what has been particularly shown and described hereinabove. Rather the scope of the disclosed invention is defined only by the claims, which follow.

The invention claimed is:

1. A method for stimulating a lacrimal gland and, optionally a meibomian gland of an eye of a user, the method comprises the following steps:

applying light stimulation pulses in the vicinity of a facial region of the eye of said user by emitting light on a retina of the eye;

activating a pupillary light reflex and one or more reflexes selected from: blink reflex; corneal reflex; menace reflex; and lacrimal reflex; and activating changes in the tear chemical composition which induce sever meibum secretion, wherein these steps are repeated as necessary to induce blinking of the eye of said user; and wherein a light intensity gradient between said light stimulation pulses and the light around the eye of said user is maintained at least 2 lumens.

2. The method of claim 1, wherein the step of applying light stimulation pulses comprises emitting light stimulation pulses at the visible spectrum of wavelength band of 350-750 nm.

3. The method of claim 1, wherein the method comprises an additional step of operating a sound source in combination with the emission of light stimulation pulses.

4. The method of claim 1, wherein the method comprises at least one additional step or a combination of the following steps:

operating a sound source;

applying vibrations to said user;

producing eyelash disturbance;

activating a rotating element in the line of sight of said user;

generating air flow towards the eye of said user; and spraying water drops towards the eye of said user.

5. The method of claim 1, wherein the method comprises generating light stimulation pulses in a random pattern.

6. A method for stimulating dry eyes by emitting light on the retina, the method comprising the steps of:

selecting a treatment plan for a specific user via an App in a mobile phone or a computer;

applying a device for stimulating the lacrimal gland and/or meibomian gland of an eye of the user in the vicinity of a facial region of the eye of the user;

generating light pulses by at least one light source and emitting said pulses towards the eye of said user;

emitting light on a retina of the eye;

activating a pupillary light reflex and one or more reflexes selected from: blink reflex; corneal reflex; menace reflex; and lacrimal reflex; and wherein a light intensity gradient between said light stimulation pulses and the light around the eye of said user is maintained at least 2 lumens.

7. A method for stimulating a lacrimal gland and optionally a meibomian gland of an eye of a user by emitting light on a retina of the eye, the method comprising the steps of:

selecting a treatment plan for a specific user via an App in a mobile phone or a computer;

interconnecting and accommodating said mobile phone in a headset;

accessing a service provider;

applying the headset in the vicinity of a facial region of the eye of a user;

operating the App to generate light stimulation pulses by at least one light source and emit said pulses towards the eye of said user;

emitting light on the a retina of the eye;

activating a pupillary light reflex and one or more reflexes selected from: blink reflex, corneal reflex, menace reflex, and lacrimal reflex; and inducing tear production; and wherein a light intensity gradient between said light stimulation pulses and the light around the eye of said user is maintained at least 2 lumens.

8. A method for stimulating dry eyes by emitting light on a retina of the eye, the method comprising the steps of:

applying a device for stimulating a lacrimal gland and, optionally a meibomian gland of an eye of a user, in the vicinity of a facial region of the eye of a user, said device comprises:

a control unit;

an optical system connected to said control unit and arranged in the viewing direction of the user, said optical system includes at least one light source, and is configured for providing light stimulation pulses to the eye of the user by said at least one light source; and a power supply unit for supplying power to said control unit and/or optical system, generating light pulses by said at least one light source and emitting said pulses towards the eye of said user;

emitting light on the retina;

activating a pupillary light reflex and one or more reflexes selected from: blink reflex, corneal reflex, menace reflex, and lacrimal reflex; and inducing tear production; and wherein a light intensity gradient between said light stimulation pulses and the light around the eye of said user is maintained at least 2 lumens.

9. The method of claim 8, wherein said light source generates light stimulation pulses in a random pattern that surprises the user.

10. The method of claim 8, wherein said optical system further comprises lens, adjustable lens and/or lens adjusting mechanism.

* * * * *